US00PP13215P2

(12) United States Plant Patent
Heims

(10) Patent No.: US PP13,215 P2
(45) Date of Patent: Nov. 12, 2002

(54) HEUCHERA PLANT NAMED 'VESUVIUS'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,947

(22) Filed: Jun. 28, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Heuchera plant characterized by its distinctive dark foliage with coral colored flowers, profuse bloom stalks, and reblooming habit.

1 Drawing Sheet

BOTANICAL CLASSIFICATION

*Heuchera sanquinea×H. americana×H. micrantha.*

VARIETY DENOMINATION

'Vesuvius'.

The present invention relates to a new and distinct hybrid of Heuchera, of the family Saxifragaceae, which originated from a cross between unknown parents. This new Heuchera was selected from seedlings grown from select plants that were open pollinated in the field in Canby, Oreg. Given its characteristics we know that at least three species are involved in its parentage; *Heuchera sanquinea, H. americana,* and *H. micrantha.*

This new Heuchera is distinguished by:

1. Dark leaves with a light silver veil or overlay.
2. Large, coral pink colored flowers.
3. Profuse number of inflorescences.
4. Repeat blooming which extends the bloom time.

The new variety has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows the new plant growing in the garden in June in Canby, Oreg.

DETAILED PLANT DESCRIPTION

The following is a detailed description of the new Heuchera hybrid based on observations of one-year old specimens grown in one gallon containers in a cool greenhouse in Canby, Oreg. The color descriptions are all based on *The Royal Horticultural Society Colour Chart.*

Plant:
- *Form.*—Basal rosette.
- *Type.*—Herbaceous perennial.

- *Hardiness.*—USDA Zones 5 to 9.
- *Size.*—18 cm tall and 42 cm wide in two years.

Stem:
- *Size.*—Found on older plants, 2 cm diameter.
- *Texture.*—Covered with brown scales.
- *Color.*—Brown 200A.

Leaf:
- *Type.*—Simple.
- *Arrangement.*—Rosette.
- *Shape.*—Orbicular to ovate.
- *Lobing/division.*—5 to 7 rounded lobes.
- *Venation.*—Palmate.
- *Margins.*—Crenate.
- *Apex.*—Mucronulate.
- *Base.*—Cordate.
- *Size.*—Grows to 8 cm long and 8 cm wide.
- *Texture.*—Leathery, puberulous. Margins and vein undersides are hirsute.
- *Petiole length.*—Grows to 12 cm.
- *Petiole texture.*—Hirsute.
- *Petiole color.*—On young leaf Greyed Purple 183D to Greyed Orange 166A to Grey Brown 199A on older leaf.
- *Leaf color.*—New leaves just opening — Greyed Purple 187A. Full size young leaves — Brown 200A with silver pink veiling in between the veins — between Greyed Purple 186A and Grey 201C. Mature leaves — Very dark brown, between Brown 200A and Black 202A with light silvering Grey 201C.

Inflorescence:
- *Type.*—Thyrse.
- *Number of flowers.*—About 100 per thyrse.
- *Peduncle.*—With 0 to 1 leaf and 1 to 2 bracts. Height — About 60 cm. Diameter — 0.15 cm. Color — Greyed Orange 177A. Texture — Hirsute.
- *First branch length.*—Grows to 2.3 cm.
- *Pedicel.*—Length — Grows to 0.4 cm at the longest. Texture — Puberulent. Color — Greyed Orange 177A.
- *Bloom period.*—June to July in Canby, Oreg.

Flower bud:
- *Size.*—0.5 cm length.
- *Description.*—Puberulent, downfacing, campanulate when opening.
- *Color.*—Coral. Red Group 51B.

Flower:

*Type*.—Perfect, zygomorphic, sepals petaloid.
*Shape*.—Campanulate.
*Size*.—0.6 cm long and 0.4 cm wide.
*Color*.—Red 48D and 51 B outside, Red 49B inside.
*Petal count*.—5, inconspicuous.
*Petal shape*.—Elliptic with a clawed base.
*Petal size*.—About 0.15 cm long.
*Petal color*.—Light pink. Red 49C.
*Calyx*.—Petaloid, divided ½ way to the base, with glandular hairs. Color as described above for flower.
*Sepal number*.—5.
*Sepal size*.—0.6 cm long and 0.4 cm wide.
*Stamen number*.—5, sterile.
*Pistil color*.—Yellow Green 145B.
*Anther color*.—Greyed Orange 170A.
*Pollen*.—None.
*Fragrance*.—None.
*Lastingness*.—A thryse blooms for about 2 weeks on the plant.

Fruit:

*Type*.—Two-beaked ovoid capsule.
*Color*.—Tan. Grey-Brown 199D.
*Fertility*—Low.
*Seeds*.—Small, elliptic in shape, black (202A) in color, typical of the genus.

Disease tolerance: Excellent disease resistance to powdery mildew, the common problem of Heuchera.

COMPARISON TO SIMILAR HEUCHERAS

Compared to Heuchera 'Veil of Passion' (U.S. Plant patent application Ser. No. 09/452,026), Heuchera 'Vesuvius' has more flowers stalks, shorter stalks, stronger reblooming, and is less veiled.

Compared to Heuchera 'Palace Passion' (unpatented), Heuchera 'Vesuvius' is earlier and longer blooming and has more flower stalks per plant. Heuchera 'Palace Passion' also is more veiled and has overlapping leaf bases unlike the new plant.

Compared to Heuchera 'Cherries Jubilee' (U.S. Plant Pat. No. 11,377), Heuchera 'Vesuvius' has darker leaves and lighter colored flowers.

I claim:

1. A new and distinct hybrid of Heuchera plant substantially as shown and described, characterized by dark foliage with coral colored flowers, profuse flower stalk number and reblooming.

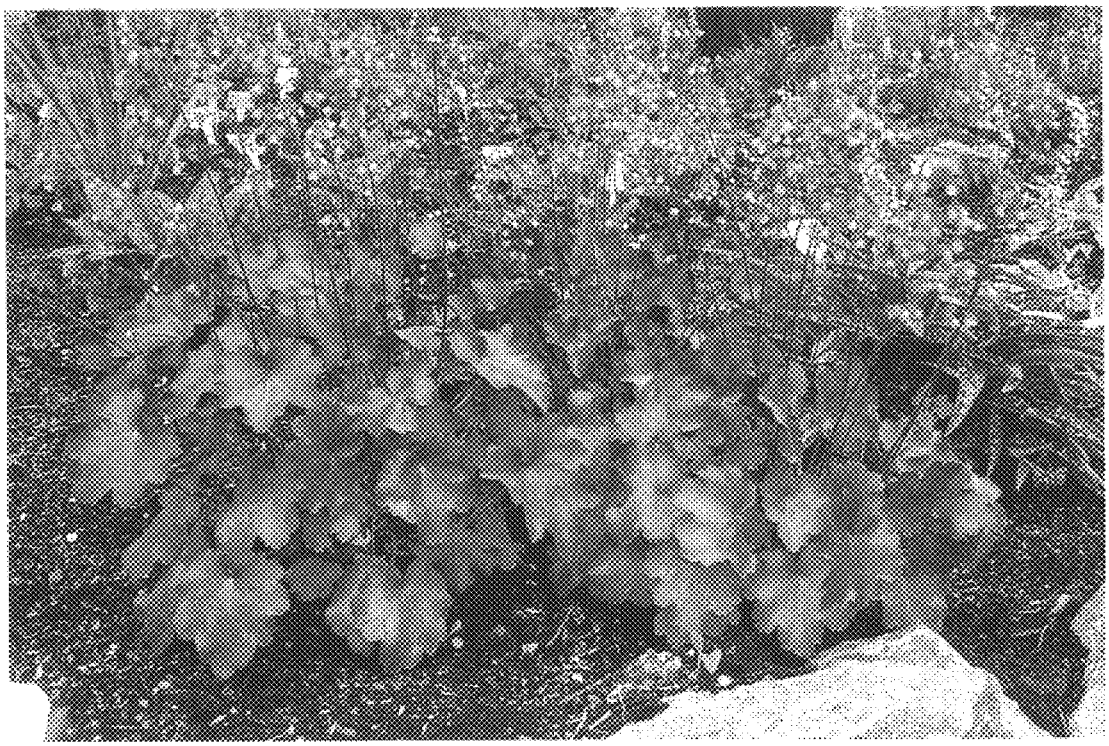

* * * * *